United States Patent
Bodenmiller et al.

(10) Patent No.: US 6,739,959 B2
(45) Date of Patent: May 25, 2004

(54) ASSEMBLY FOR THE MANUFACTURE OF MEDICAL, DENTAL-MEDICAL, DENTAL-TECHNICAL AND TECHNICAL PARTS FROM CERAMICS

(75) Inventors: Anton Bodenmiller, Leutkirch (DE); Pius Steinhauser, Leutkirch (DE)

(73) Assignee: Kaltenbach & Voigt GmbH & Co., Biberach (DE)

( * ) Notice: Subject to any disclaimer, the term of this patent is extended or adjusted under 35 U.S.C. 154(b) by 0 days.

(21) Appl. No.: 10/261,469

(22) Filed: Oct. 2, 2002

(65) Prior Publication Data

US 2003/0031977 A1 Feb. 13, 2003

Related U.S. Application Data

(62) Division of application No. 09/735,810, filed on Dec. 14, 2000, now Pat. No. 6,495,073, which is a continuation of application No. PCT/EP00/00404, on Jan. 19, 2000.

(30) Foreign Application Priority Data

Apr. 16, 1999 (DE) .......................... 199 17 324
Jul. 2, 1999 (DE) .......................... 199 30 564

(51) Int. Cl.[7] .............................................. B24B 41/06
(52) U.S. Cl. ....................................... 451/364; 451/397
(58) Field of Search ........................... 451/29, 30, 364, 451/365, 385, 379, 377, 397, 398, 394, 28

(56) References Cited

U.S. PATENT DOCUMENTS 1,297,660 A * 3/1919 Collins ........................ 351/174
2,166,037 A * 7/1939 Campos ....................... 451/240
5,192,472 A   3/1993 Andersson ................... 264/40.1
5,215,693 A   6/1993 Lee .............................. 264/128
5,776,408 A * 7/1998 Ghosh et al. ................ 264/400
6,106,747 A   8/2000 Wohlwend ................... 264/16

FOREIGN PATENT DOCUMENTS

| EP | 0 030 850 A1 | 6/1981 |
| EP | 0 375 647 B1 | 6/1990 |
| EP | 0 389 461 B1 | 11/1993 |
| EP | 0 580 565 A2 | 1/1994 |

OTHER PUBLICATIONS

V.D. Hennige, H.–J. Ritzhaupt–Kleissl and J.H. Housselt, "Verfahren zur Herstellung schrumpffreier $ZrSiO_4$–Keramiken", Keramische Zeitschrift 50 [4] 1998, ppp. 262–265.

* cited by examiner

Primary Examiner—Hadi Shakeri
(74) Attorney, Agent, or Firm—Fitzpatrick, Cella, Harper & Scinto

(57) ABSTRACT

For the manufacture of shaped parts (6) from ceramics, for example for dental-technical purposes, an assembly is provided which comprises a powdery ceramic raw material compressed to form a ceramic green compact (4), an embedding mass (3) which neither damages nor reacts chemically with the ceramic green compact (4), and a holder or workpiece receiver (1) which holds the embedding mass (3) in a manner to allow the ceramic green compact (4) to be machined while being embedded in the embedding mass.

1 Claim, 3 Drawing Sheets

ASSEMBLY FOR THE MANUFACTURE OF MEDICAL, DENTAL-MEDICAL, DENTAL-TECHNICAL AND TECHNICAL PARTS FROM CERAMICS

CROSS REFERENCE TO RELATED APPLICATIONS

This is a Division of U.S. patent application Ser. No. 09/735,810, filed Dec. 14, 2000, now U.S. Pat No. 6,495,073, which is a Continuation of International Application PCT/EP00/00404, filed Jan. 19, 2000 which in turn claims priority of German applications DE 199 17 324.9, filed Apr. 16, 1999 and DE 199 30 564.1, filed Jul. 2, 1999, the priorities of which are hereby claimed, said International Application having been published in German, but not in English, as WO 00/62705 Oct. 26, 2000.

BACKGROUND OF THE INVENTION

1. Field of the Invention

The invention relates to an assembly for the manufacture of shaped parts from ceramics, in particular for medical or dental-medical purposes.

2. Description of the Related Art

In medical engineering, dental medicine or dental engineering, prosthetic parts have hitherto been manufactured mainly from high-quality precious metal alloys, cobalt chromium alloys and partially also from titanium. Due to the necessary bio-compatibility of such medical products, the metal surfaces of these prosthetic parts are usually coated with ceramic substrates. In dental medicine and dental engineering a veneering with dental porcelains, in particular in the anterior tooth region, often takes place for mainly aesthetic reasons.

For a fairly long time, efforts have been made to substitute these metal alloys with completely ceramic systems. However, this requires the use of high-performance ceramics, as are used in industrial ceramics partially with industrially manufactured serial products. In contrast with the industrially manufactured ceramic parts, however, the prosthetic workpieces manufactured in medical engineering or dental engineering are in each case unique, which is why, for economical, material-technical and industrial reasons, the known industrial production methods cannot be used. A further known problem of such high-performance ceramics is the partially great contraction of the ceramic pastes during sintering, which can amount to up to 20%. However, such dimensional changes cannot be tolerated with dental-technical shaped parts, because, for example with bridgework, the distances between the columns (stumps) or the height of the contact points to the antagonist, must be kept within the micrometer range.

For this reason, several attempts have been made to machine prosthetic parts from solid ceramic blocks, the sintering of which is complete (semifinished material), directly by way of machining with geometrically defined cutting edges, machining with geometrically undefined cutting edges or by way of erosion by means of ultrasound erosion or lasers.

The grinding-out or milling of ceramic parts with the aid of diamond tools, for example with the so-called CAD-CAM method, has become generally accepted in practice—although only to a limited extent. With this method, first of all a measurement is taken of the tooth stump, and subsequently of the crown provided thereon, which is available, for example, as a wax model. The data is then entered into a CAD program which controls a milling machine. This milling machine then automatically machines the sintered and high-strength ceramic block. However, expenditure for this is extremely high because the ceramic block which is already sintered is extremely hard. If, for example, high-performance ceramics such as aluminum oxide ($Al_2O_3$) or zirconium oxide ($ZrO_2$) are ground, the diamond tools wear out very quickly, resulting in geometry tolerances on the workpiece because the geometry and the diameter of the tools change during the machining. Moreover, at critical points of the prosthesis parts, for example at crown edges, material eruptions or micro-tears can arise. A further problem is represented by the long grinding time, because work can only be done at low eroding rates and at reduced rate of feed, because otherwise great stresses in the material can arise, which can lead in turn to hairline cracks and the like. Moreover, a separating step is necessary, where, at the end of the machining, the milled-out crown is separated from the rest of the ceramic block. With this manual separating and grinding procedure, both geometry errors and material eruptions can arise, with the result that the expensively manufactured part can possibly no longer be used. Finally, the machining of high-performance ceramics requires expensive and automatically operating grinding or milling machines because the dental technician or machine operator can no longer manually control the machining parameters (feed, delivery) at all. Alternatively to the high-performance ceramics, modified dental ceramics can, admittedly, also be used, which permit a still economical grinding machining, but these modified ceramics then also only have reduced strength values.

Alternatively to the machining of ceramic blocks which are already sintered and which are high-strength, methods have therefore been developed, where the ceramic shaped parts are manufactured from a ceramic raw material which is not yet sintered or from presintered material. With two known methods, first of all an impression is made of the machined tooth stump and then a positive is formed, which for its part consists of fire-proof material, in particular ceramics. A tooth crown of wax is formed on to this positive stump, the tooth crown of wax simulating the final shape of the crown. Subsequently, the positive stump, with the wax crown located thereon, is placed upon a rubber base which forms the floor for a rubber ring, with this rubber ring surrounding the positive stump with the wax crown with clearance. A liquid or plastic embedding mass is then introduced into the muffle form formed in this way, the embedding mass surrounding the positive stump with the wax crown apart from a pouring channel. This pouring channel is formed, for example, by a wax cone which is connected to the wax crown.

After the hardening of the embedding mass, the rubber foundation and the rubber ring are removed, so that the hardened embedding mass with the filling wax cone is freely available. This unit is then put into an out-waxing and preheating furnace so that the wax of the wax crown is expelled by way of the filling vent. In this way a cavity corresponding to the wax crown is formed in the embedding mass.

The embedding mass with the cavity located therein and a sintered porcelain blank are then introduced together into a preheating furnace and heated to about 800° C. At this temperature the sintered porcelain blank becomes plastic, whereas the embedding mass itself hardens. After the removal of the embedding mass and the plastic porcelain blank from the furnace, the now plastic porcelain is introduced by way of the filling opening into the cavity by means of a pressing device. This pressing-in itself takes place in a special pressing-in furnace. After the cooling of the porcelain mass, the embedding mass is then destroyed so that the crown with the filling vent located therein becomes free. As a concluding step, finally the separation of the crown from the filling vent, which has arisen in the pouring channel, and a final external machining take place.

With this method also there is the danger that tears can arise in the crown upon separation of the porcelain crown from the filling vent. The use of an already sintered porcelain blank guarantees that no more shrinkage occurs with the crown if it is subsequently fired again in the baking oven. In contrast with ceramics, porcelain which is already sintered can again be plasticized upon heating to about 800° C., this no longer being possible with ceramics even at extremely high temperatures. However, compared with porcelain, ceramics have considerably greater bending strength. The manufacture of two or more crowns which are connected to each other by way of a connecting bar, is, for example, not possible with porcelain, because this connecting bar would break. Such complicated dental-technical shaped parts can therefore only be manufactured with ceramic material. This is the reason why porcelain is usually only used for inlays, onlays or single crowns.

The method currently most widespread in dental engineering for the manufacture of ceramic crowns is the so-called slip method. In this respect, an impression is first of all made of the machined tooth stump and then a metal frame, in particular of gold, titanium or the like, is prepared. This metal frame consists of a thin layer fitting the tooth stump and finally produces a cup-shaped part. Ceramic material is then applied to this frame in plastic form (slip) in several layers, with a firing of the metal frame with the applied ceramic slip taking place in each case after the application of a layer. In this way the crown is coated unevenly on the outside and is adapted to the teeth. In this respect, the ceramic slip is applied to the metal frame with a brush, but has the disadvantage that it contains a high content of liquid, in particular water, which leads to a shrinkage of the material during firing. This shrinkage can only be calculated with difficulty, for which reason the ceramic mass must also be applied in several layers.

A further method for the manufacture of dental ceramic parts, where the shrinkage of the ceramic material is considered, is described in EP 0 389 461 B1. Here it is suggested to first of all prepare by way of an impression a negative copy of the surface of the machined tooth stump and subsequently to machine an isostatically compressed ceramic green compact by means of copy-milling. During the copy-milling, the sinter shrinkage is considered, in that the surface of the machined green compact is enlarged somewhat in order to offset the subsequent shrinkage again. In the process, however, by way of the copy-milling only the underside of the ceramic green compact is machined, the upper side of the shaped part also being covered after the sintering with a porcelain layer and being brought into the final shape. In a similar manner it is also suggested in EP 0 375 647 B1 to machine a ceramic green compact before the sintering by way of milling.

However, the machining of such a green compact turns out to be quite difficult because the compressed material is very brittle. The two publications named previously give no information as to how these difficulties can be overcome. In a further development, therefore, in EP 0 580 565 A2 it is suggested to compress the powdery ceramic raw material against the surface of a positive copy of the machined tooth stump. In this respect, in turn the positive copy is enlarged compared with the tooth stump in order to compensate for the shrinkage. Here also the surface of the ceramic shaped part is covered with a porcelain layer.

In order to avoid this shrinkage of the ceramics during sintering, the shrinkage being difficult to calculate, in EP 0 030 850 the use of a shrinkage-free ceramic material is suggested. In this respect, the raw material is pressed or poured in powdery or in liquid form into a prefabricated casting mold, the structure of which corresponds substantially with the shape of the ceramic part to be manufactured, or is in turn pressed against a stamp which is an exact copy of the tooth stump. As with the other methods, here also therefore, first of all a very costly manufacture of an appropriate casting mold is necessary.

SUMMARY OF THE INVENTION

It is therefore the object of the present invention to provide a simple and economical assembly for the manufacture of shaped parts of ceramics, which can be carried out, for example, by a dentist or dental technician directly in a medical laboratory, practice laboratory or commercial laboratory.

The object is achieved by an assembly which includes a powdery ceramic raw material compressed into a ceramic green compact, an embedding mass of an easily machinable material that does not damage or chemically react with the material of the ceramic green compact, the ceramic green material being embedded in the embedding mass, and a holder which holds the embedding mass in a manner to allow the ceramic green compact to be machined while being embedded in the embedding mass.

In the assembly in accordance with the invention, first of all the powdery ceramic raw material is compressed to form a ceramic green compact, this ceramic green compact is then machined by means of eroding methods and is subsequently sintered to form a high-strength ceramic shaped part, with the green compact being embedded before the machining into a workpiece receiver by means of an embedding mass, which neither damages nor reacts chemically with the green compact. The initially powdery ceramic raw material is only put by the compressing into a state where it can be machined at all. The state of the ceramic green compact is then similar to that of chalk, that is to say, in comparison with already sintered ceramic blocks it can be machined substantially more easily, more quickly and with little abrasion of the tools and accordingly much more accurately. By way of the embedding in accordance with the invention, the ceramic green compact is both fixed and supported during the machining, so that no erupting of thin walls or other damage is to be feared and it can therefore be effectively and accurately machined. A further advantage of this consists in that excess raw material, which is removed by milling during machining of the ceramic green compact, can be recovered again and reused, with the material expenditure being clearly reduced as a result. As the machining tools are also stressed less and therefore achieve a longer service life, the method in accordance with the invention is to be regarded as substantially more economical compared with the known methods, where ceramic blocks which are already sintered are machined. According to the invention, in medicine, dental medicine and dental engineering, biocompatible implant parts, inlays, partial crowns, crowns, bridges, prosthesis bases or auxiliary parts can be economically manufactured accurately and with high mechanical strength adapted to the purpose of use. In particular, with this invention there is the possibility of bringing a ceramic green compact, the original shape of which has nothing in common with the final structure of the ceramic shaped part to be manufactured, exclusively by way of machining by means of eroding methods, into the desired final shape, without compressing the material as in the known methods—into a casting mold or against a stamp.

Further developments of the invention are described in detail hereinafter. An essential aspect of this invention lies in the selection of the ceramic raw material. This should shrink as little as possible during the sintering, and in the ideal case should be almost shrinkage-free. A ceramic material which fulfils these conditions is, for example, zirconium ($ZrSiO_4$), the properties of which will be described in more detail. However, it would also be conceivable to use the already known and frequently used ceramics zirconium oxide ($ZrO_2$) or aluminum oxide ($Al_2O_3$). These shrink to a certain degree during the sintering. However, the ceramic green compact usually compressed to form a cube or to be box-shaped, has an extremely even material density, so that it is to be expected that the material shrinks evenly and therefore foreseeably during the sintering. In contrast with the known methods, where, for example, the powder is pressed into a casting mold or is poured in under pressure, and where, therefore, an uneven density distribution of the raw material is often not to be avoided, with the method in accordance with the invention the shrinkage process can be taken into account very easily and can be compensated for by manufacturing larger shaped parts before the sintering.

Also described herein are advantageous embodiments for facilitating the machining of the ceramic green compact. The ceramic green compact is preferably machined with the aid of an eroding machine—for example a milling, turning, drilling or grinding machine, with the machining being able to take place automatically. The corresponding control commands for the eroding machine can then be contained in a special erosion program which is prepared, for example, on the basis of a three-dimensionally measured positive model of the tooth stump and the tooth crown. In this respect, when preparing the erosion program, parameters such as, for example, a desired cement gap width or a possible shrinkage factor of the raw ceramic material can be considered. A suitable milling wax, for example, can be used as embedding mass. The machining of the green compact can take place in several steps in which, in each case, certain areas of the green compact are machined, with the areas of the green compact, which have already been machined previously, being surrounded again with the embedding mass and thereby being stabilized. In this way the very thin side walls of ceramic crowns can therefore be protected during the machining. By melting the milling wax, after the machining the ceramic green compact can then be carefully extracted again. This milling wax and the embedding mass can also be collected during the machining of the green compact and reused.

The properties of three preferably used ceramic materials are now to be discussed.

The very frequently used aluminum oxide ($Al_2O_3$) is also known by the name corundum. In addition to many and diverse possibilities of using this material in industry (for example as abrasives, grinding materials, fire-proof materials), aluminum oxide is a very frequently used oxide in most varied clay minerals and ceramics which are used in the case of ceramic tooth replacement, but also in flower vases or coffee-cups. Aluminum oxide is in particular a material suitable for tooth replacement because it has a tooth-colored appearance, high resistance to abrasion, chemical resistance, biological compatibility and a pleasant contact feeling with pickled or polished ceramic surfaces. A further advantage is also to be seen in that aluminum oxide is X-ray translucent and tooth crowns consisting of it do not cause any artefacts during X-ray examinations, which could lead to misinterpretations of the X-ray image.

Zirconium oxide ($ZrO_2$) can occur in several different crystal modifications. As zirconium oxides have, among the known ceramic materials, the highest bending strength and tensile strength values, high resistance to wear and resistance to corrosion and low thermal conductivity, in recent years they have become increasingly significant in the technical and medical field. As a result of their excellent properties, zirconium oxide ceramics are preferably used for components which can be greatly mechanically loaded. Moreover, zirconium oxide displays only relatively little contraction during the sintering.

On the basis of zirconium oxide ($ZrO_2$), with the aid of a reaction sintering method, $ZrSiO_4$ ceramics, which are almost shrinkage-free, can be manufactured. This is achieved in that a reactive component contained in the raw ceramic green compact enlarges its volume during the sintering and therefore compensates for the shrinkage of the remaining components. A method of this kind which is suitable for zirconium oxides is described, for example, in the article "Verfahren zur Herstellung schrumpffreier $ZrSiO_4$-Keramiken" ("Method for the manufacture of shrinkage-free $ZrSiO_4$-ceramics") of the Keramische Zeitschrift (Ceramics Journal) 50 (4) 1998. In this case an intermetallic compound (zirconium disilicide, $ZrSi_2$) is used as reactive component. In addition, polysiloxane, a so-called low-loss binder, is used as pressing aid, which reacts during the sintering with the zirconium disilicide and the zirconium oxide to form the desired ceramics ($ZrSiO_4$). The essential advantage of this reaction sintering method consists in that the sinter shrinkage to be expected, which is a function of the portion of the various reaction components, can be estimated with the aid of a simple calculation. The required content of the reactive component, that is to say of the zirconium disilicide ($ZrSi_2$), can then be calculated, where a shrinkage of almost 0% occurs.

As a result of the properties just described, with these $ZrSiO_4$-ceramics micro-structured components can be manufactured, the dimensions of which are identical before and after the sintering. A mechanical finishing, which is often not at all possible with very small detail structures without damaging the workpiece, is then no longer necessary. For the same reasons, these ceramics are therefore also excellently suitable for the manufacture of dental-medical or dental-technical parts, in particular of tooth crowns with thin walls.

As a result of their properties, the three ceramic materials just named are particularly well suited for use in the dental-medical field. Nevertheless, the method in accordance with the invention is not restricted to these materials, but can also be used with other ceramic materials, for example with magnesium oxide (MgO), aluminum titanate (ATi) or piezo-ceramics (PZT), not only in medical, but also in technical fields. In this respect, the use of a shrinkage-free ceramic material is indeed particularly advantageous, but in no way absolutely necessary because—as already noted—by way of the even compression of the material to form a green compact, a homogeneous density distribution, and accordingly an even and therefore controllable shrinking of the shaped part during the sintering, is achieved.

BRIEF DESCRIPTION OF THE DRAWINGS

The invention will be explained in more detail in the following with reference to the enclosed drawings which show the individual steps of a method in accordance with the invention for the manufacture of a tooth crown.

An advantage of the method described in the following consists in that in principle it is very similar to the hitherto known methods for the manufacture of tooth crowns and can therefore be carried out very easily by a dental technician.

DETAILED DESCRIPTION OF THE PREFERRED EMBODIMENT

In this respect, first of all, for example on the basis of an impression, the dental technician makes a positive model of the machined tooth stump from gypsum or another suitable modeling material as the foundation of his prosthetic work. This positive model is then measured three-dimensionally in a measuring device mechanically, optically or according to another method. By way of special software, a milling or erosion program for machining the inside of the crown, the structure of which corresponds to the shape of the tooth stump, is then generated and loaded into the control of an automatic milling machine. In the process, the dental technician can enter additional parameters, for example a necessary cement gap width, which are considered by the software during the preparation of the milling program. Moreover, for ceramics which contract during sintering, corresponding correction factors can be considered, in order to compensate for the contraction by preparing slightly enlarged shaped parts.

Figure 1:
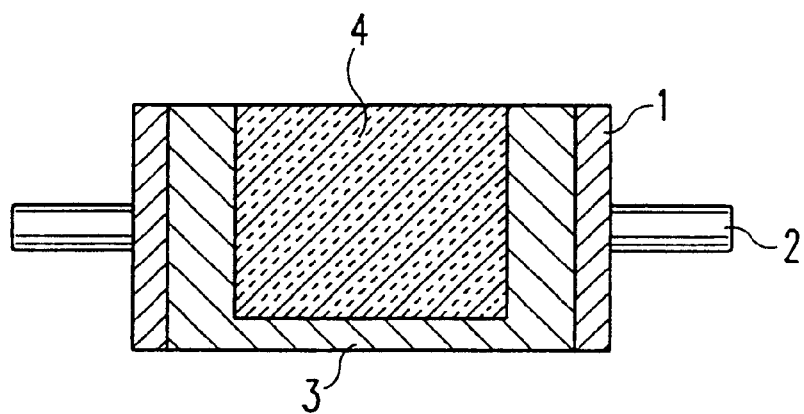
FIG. 1 shows a green compact inserted into a workpiece receiver.

As shown in FIG. 1, the dental technician then inserts an isostatically compressed ceramic green compact 4, for example of a shrinkage-free ceramic material, of aluminum oxide ($Al_2O_3$), zirconium oxide ($ZrO_2$) or another high-performance ceramic, into a workpiece receiver 1 provided with an axis of rotation 2. In this respect, the securing of the green compact 4 in the workpiece receiver 1 takes place by way of its embedding with a preferably pourable embedding material 3, which fixes the green compact 4 mechanically, but, in the process, does not damage the ceramic compressed composite or change the ceramic raw material by way of any chemical reactions. For example a special milling wax can be used as a reasonably-priced, easily millable embedding material 3 which is suitable as supporting body.

Figure 2:
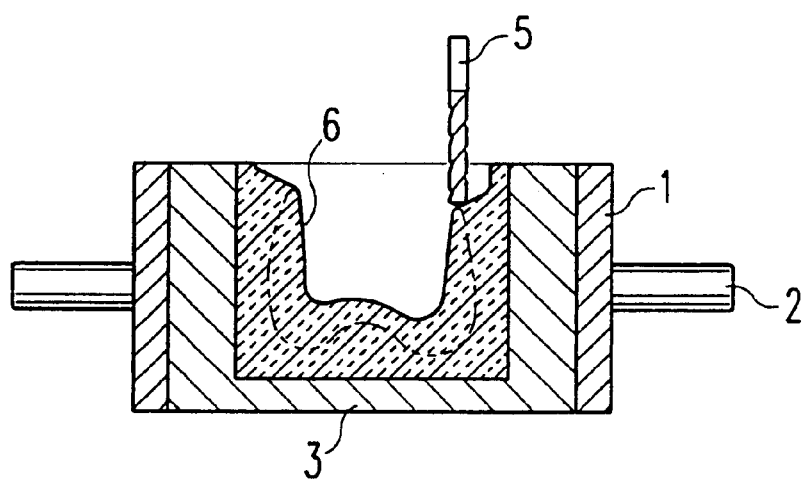
FIG. 2 shows the manufacture of the inside of the crown.

In the next step, which is shown in FIG. 2, the workpiece receiver 1 is inserted into the holding device of a milling machine and the milling procedure is started, whereby in the present case first of all the milling-out of the inside of the crown of the workpiece 6 takes place. The control of the miller 5 preferably takes place fully automatically with the aid of the milling and erosion program. However, with the use of shrinkage-free ceramics it would also be conceivable to carry out the milling manually, for example by way of a direct copying of the positive model of the stump. However, in this case the positive model would then have to be coated with a spacing lacquer or provided with a foil cap in order to take into account the necessary cement gap width.

If the milling procedure takes place fully automatically, the dental technician can in the mean time, as usual, model the crown or another dental-technical work in wax. This work, the modeling of which is complete—disposed on the work foundation (the tooth stump or the positive model)—is again measured three-dimensionally in the measuring device in order to ascertain the required structure of the finished tooth crown.

Figure 3:
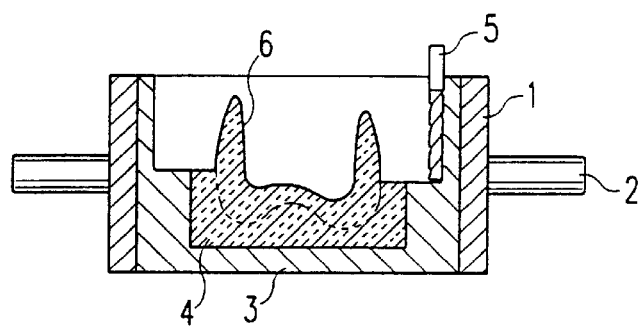
FIG. 3 shows the manufacture of the first area of the outside of the crown.
Figure 4:
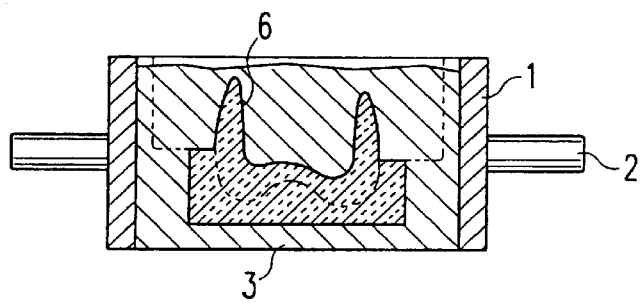
FIG. 4 shows the re-embedding of the side already machined.
Figure 5:
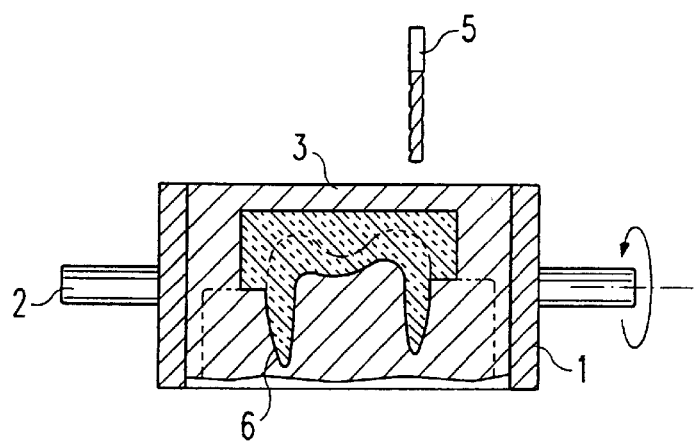
FIG. 5 shows the workpiece receiver rotated by 180°.

As previously, with the aid of the software a milling program for the machining of the outside of the crown is then generated and loaded into the control of the milling machine. In the example shown, the milling program is then divided into two steps, in which in each case the areas going as far as the equator of the crown (from the crown edge to the equator or from the occlusal surface as far as the equator) are machined. The first step of this milling program, in which the outside of the crown is machined from the lower crown part as far as the equator, is shown in FIG. 3. The side of the crown 6 which is not yet machined at this instant is, in this respect, as before, supported by the embedding mass 3 and the green compact 4 is therefore prevented from falling out of the workpiece receiver 1. After the machining of the underside of the workpiece 6 is completed, the embedding mass 3 is subsequently once again poured into it (FIG. 4). It would also be possible to fill up the previously milled-out inside of the crown with the milling wax 3 again already before the machining of this first area of the outside of the crown, in order to support the side walls of the crown. Subsequently, by rotating the workpiece receiver 1 by 180°, the upper side of the crown which is still to be machined is repositioned into a position suitable for the milling (FIG. 5).

Figure 6:
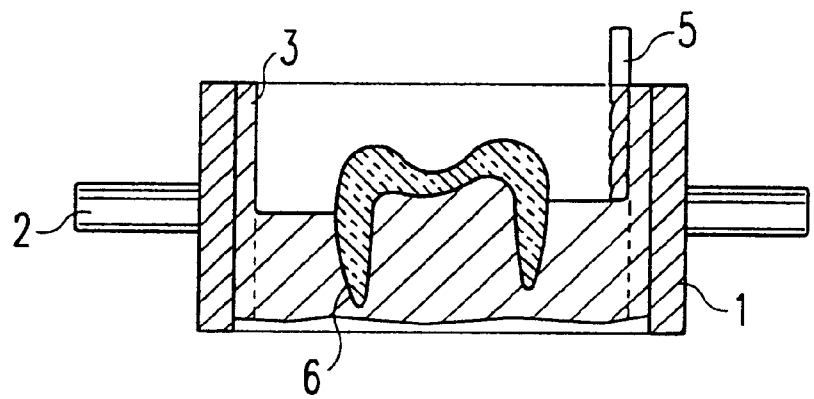
FIG. 6 shows the manufacture of the second area of the outside of the crown.

According to the representation in FIG. 6, in the second step of the milling program the outer upper part of the crown is then milled from the occlusal surface as far as the equator. The underside of the workpiece, which is unstable and slightly fragile in this state, is also held securely during this machining step by way of further embedding into the milling wax 3 and is supported at the critical points (the partially very thin side walls of the workpiece 6), so that no material eruptions of or damage to the workpiece 6 are to be feared. Moreover, by way of the embedding mass 3 being poured once again into the primary side of the green compact, the workpiece 6 is prevented from falling out.

During the entire work, the milled-off green compact and embedding material can be drawn off by suction. In an appropriately constructed dust extraction system the loose and powdery green compact material can then be separated from the milling wax 3 and recovered again. The dental technician can then, in turn, press new green compacts from this recovered material in a suitable device, so that an optimum yield of ceramic shaped parts can be achieved from the ceramic base material.

Figure 7:
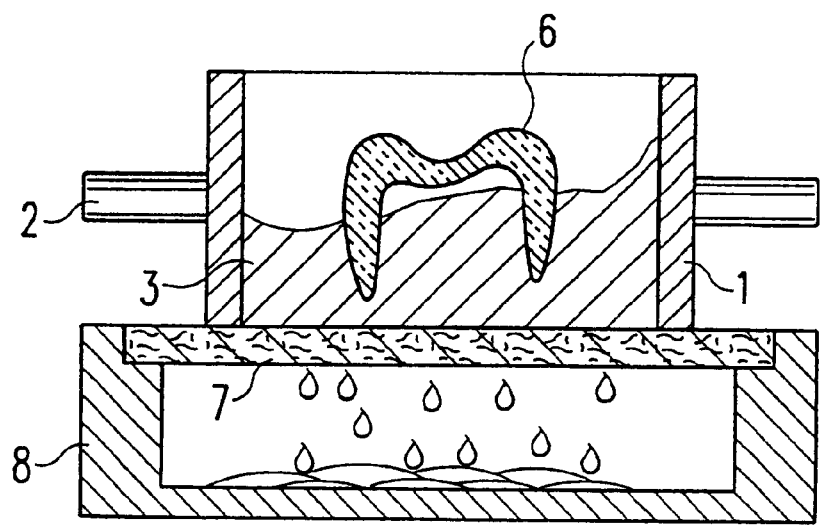
FIG. 7 shows the extraction of the green compact.

After the end of the milling procedure, the green compact workpiece 6 is extracted. With the use of milling wax, this working step takes place, for example, by means of a hot-air drier, in a heating furnace or a special waxing-out device shown in FIG. 7. In this respect, the workpiece receiver 1 with the green compact workpiece 6, which is still supported in a remaining portion of the embedding mass 3, is placed on to a fluid mat 7 which forms the upper side of a collecting dish 8. During the supply of heat, the milling wax then melts and drips through the fluid mat 7 into the collecting dish 8, so that finally the green compact workpiece 6 lies fully extracted on the fluid mat 7. The molten milling wax collected in the collecting dish can then be reused in exactly the same way as the powdery ceramic raw material already recovered previously.

In the laboratory, the sintering of the milled-out workpiece 6 to form the high-strength prosthetic part then finally takes place in a suitable ceramic furnace.

The method just described represents a particularly advantageous use of the invention. In this respect, the individual steps are designed in such a way that the green compact is machined as carefully as possible in order to avoid the occurrence of material eruptions or tears. However, modifications are also conceivable. For example, the sequence of the machining of the inside of the crown and the outside of the crown could also be reversed. Moreover, it would be conceivable to prepare only the inner or outer contours of the workpieces and then also to machine them in another way. However, the shape of the green compact, the machining of which is complete, preferably already corresponds to the desired end shape of the ceramic shaped part (in particular with shrinkage-free ceramics) or, with ceramics which shrink to a certain degree, this shrinkage factor is considered in such a way that during the sintering the green compact shrinks in such a way that the finished shaped part has the desired end shape, so that a costly finishing, which is unprofitable from the commercial point of view, is omitted. However, if it is desired for aesthetic reasons or if it is necessary, only the partial contours of the final shape can be prepared, with the final contours then being prepared by way of veneering by means of porcelain or another suitable material. Finally, according to the shape of the ceramic shaped part to be manufactured, in place of the milling machine, or in addition to it, other eroding machines, for example turning, drilling or grinding machines, can also be used.

The essential advantage of the invention lies in that by way of the machining of a workpiece from a green compact which can be machined easily and reliably, the hitherto known great machining problems—the high level of tool wear, accuracy and demands on the milling machine and therefore also the manufacturing costs—are considerably reduced. This is in particular of advantage if medical-technical or dental-medical prosthetic workpieces are to be manufactured, where they are unique and therefore cannot be manufactured in large piece numbers. Nevertheless, the invention also offers great advantages in the manufacture of technical parts, because very small parts can also be manufactured with an accuracy which has hitherto not been achieved.

What is claimed is:

1. An assembly for the manufacture of ceramic shaped parts, said assembly comprising:

a powdery ceramic raw material compressed into a ceramic green compact;

an embedding mass of an easily machinable material that does not damage or chemically react with the material of said ceramic green compact, said ceramic green material being embedded in said embedding mass; and a holder which holds said embedding mass in a manner to allow said ceramic green compact to be machined while being embedded in said embedding mass.

\* \* \* \* \*